United States Patent [19]

Einzig

[11] Patent Number: 4,873,989

[45] Date of Patent: Oct. 17, 1989

[54] FLUID FLOW SENSING APPARATUS FOR IN VIVO AND INDUSTRIAL APPLICATIONS EMPLOYING NOVEL OPTICAL FIBER PRESSURE SENSORS

[75] Inventor: Robert E. Einzig, Herndon, Va.

[73] Assignee: Optical Technologies, Inc., Herndon, Va.

[21] Appl. No.: 915,113

[22] Filed: Oct. 3, 1986

Related U.S. Application Data

[63] Continuation-in-part of Ser. No. 587,464, Mar. 8, 1984, abandoned, and a continuation-in-part of Ser. No. 776,118, Feb. 25, 1985.

[51] Int. Cl.[4] ............................................. A61B 5/02
[52] U.S. Cl. ............................... 128/692; 73/861.42; 73/861.52; 356/345; 356/352
[58] Field of Search ........... 73/861.42, 861.52, 861.61, 73/861.62; 128/672, 673, 675, 691, 692, 345, 352; 372/30, 32

[56] References Cited

U.S. PATENT DOCUMENTS

| | | | |
|---|---|---|---|
| 2,650,487 | 9/1953 | Renwanz | 73/861.67 |
| 3,724,503 | 4/1973 | Cooke | 73/861.63 |
| 4,025,875 | 5/1977 | Fletcher et al. | 372/30 |
| 4,150,342 | 4/1979 | Johnston, Jr. et al. | 372/32 |
| 4,240,294 | 12/1980 | Grände | 128/673 |
| 4,256,094 | 3/1981 | Kapp et al. | 128/675 |
| 4,418,981 | 12/1983 | Stowe | 356/345 |
| 4,442,350 | 4/1984 | Rashleigh | 324/96 |
| 4,508,103 | 4/1985 | Calisi | 128/673 |
| 4,515,430 | 5/1987 | Johnson | 350/96.12 |
| 4,533,247 | 8/1985 | Epworth | 356/345 |
| 4,534,222 | 8/1985 | Finch et al. | 356/345 |
| 4,562,744 | 1/1986 | Hall et al. | 73/861.61 |
| 4,563,646 | 1/1986 | Désormière | 350/375 |
| 4,583,228 | 4/1986 | Brown et al. | 372/32 |
| 4,593,701 | 6/1986 | Kobayashi et al. | 128/673 |
| 4,608,697 | 8/1986 | Coldren | 372/32 |
| 4,609,290 | 9/1986 | Cahill | 356/345 |
| 4,621,646 | 11/1986 | Bryant | 128/673 |
| 4,622,672 | 11/1986 | Coldren | 372/32 |
| 4,699,513 | 8/1987 | Brooks et al. | 356/345 |

FOREIGN PATENT DOCUMENTS

| | | | |
|---|---|---|---|
| 554115 | 11/1981 | France | 78/861.61 |
| 2492562 | 4/1982 | France | 128/672 |
| 1043647 | 3/1955 | Netherlands | 73/861.53 |
| 885894 | 11/1981 | U.S.S.R. | 73/861.42 |
| 8503855 | 9/1985 | World Int. Prop. O. | 73/705 |

OTHER PUBLICATIONS

"Integrated Signal Conditioning for Silicon Pressure Sensors" by Borky et al., IEEE Trans. on Electron Devices, vol. 26, No. 12, 12/79, pp. 1906–1910.
"Methods of Flow Measurement" by Grey et al., J. of the Am. Rocket Society, May–Jun. 1953, pp. 133–134.
"Wavelength Monitoring of Single–Mode Diode Laser Using Guided Wave Interferometer" by Sheen et al.; Optics Letters; vol. 5, No. 5, 5/80, pp. 179–181.
"Methods of Flow Measurement": by J. Grey et al.; J. of the Amer. Rocket Soc. 6/1953; pp. 133–134.
"A Catheter Flow Probe . . . Source Parameters" by Min et al., IEEE Trans. on Biomed. Eng.; vol. BME26, #9; Sep. 1979, pp. 509–512.
"Integrated Signal Conditioning for Silicon Pressure Sensors" by Borky et al.; IEEE Trans. on Electron Devices; ED26, #12, 12/79, pp. 906–910.

Primary Examiner—Lee S. Cohen
Assistant Examiner—David Shay
Attorney, Agent, or Firm—Kerkam, Stowell, Kondracki, & Clarke

[57] ABSTRACT

A fiber optical fiber fluid flow measuring device is provided for in vivo determination of blood flow in arteries. The device includes a fiber optical fluid differential pressure measuring device having at least one optical fiber sensor which optical fiber sensor is positioned in the blood flow passage in a restricted flow area. The fiber optical differential pressure fluid sensor is connected to a divided interferometer associated with an opto-electronic demodulator which has an output signal representing the differential pressure in the sensed area. The device also has utility in industrial applications.

16 Claims, 11 Drawing Sheets

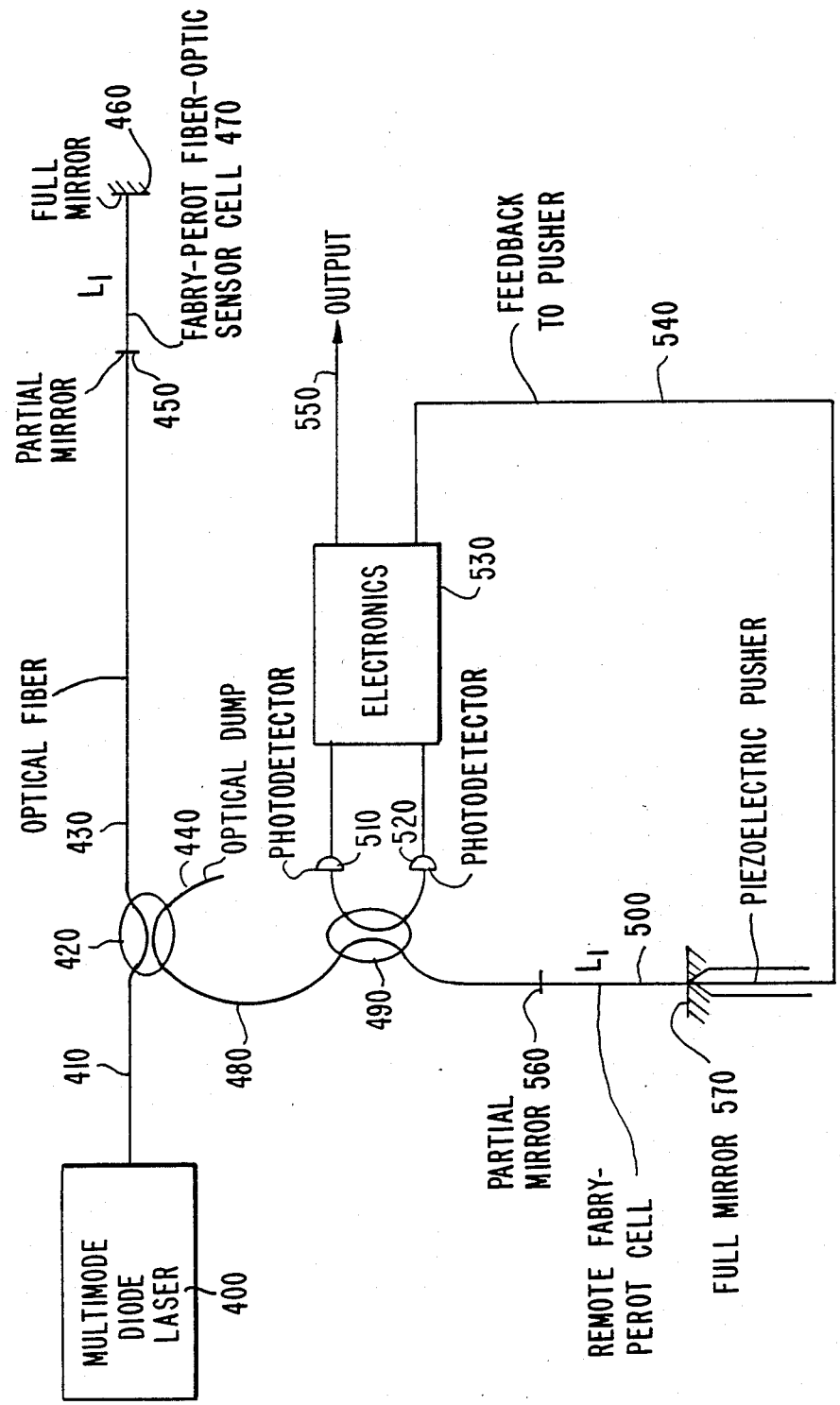

FLUID FLOW SENSING APPARATUS FOR IN VIVO AND INDUSTRIAL APPLICATIONS EMPLOYING NOVEL OPTICAL FIBER PRESSURE SENSORS

INTRODUCTION

This application is a continuation-in-part of application Ser. No. 587,464 filed Mar. 8, 1984 now abandoned and Application Ser. No. 776,118 filed Feb. 25, 1985 based on PCT/US85/00295.

This invention is directed to means for measuring fluid flow in arteries and veins of mammals wherein the measurements are provided by differential pressure sensing means positioned in the fluid conduit. With the differential pressure and the knowledge of the cross-sectional area of the conduit, flow rates can be determined. In in vivo flow rate measurements, the diameter of the artery is determined using one of several techniques, such as direct measurement with a probe, two differential pressure measurements, by dye or thermal dilution methods, and by means of x-rays. The invention also has industrial application.

BACKGROUND OF THE PRIOR ART

Means to measure pressure in the human blood stream by a number of techniques are known. However, blood pressure alone fails to provide answers to many questions, such as: whether sufficient volume of blood to satisfy body needs is flowing, the condition of arteries and veins, and the existence of partial blockages that reduce blood flow to critical areas of the body. It is only by determining actual rate and volume of flow that the medical practitioner is provided with greater insight into the actual condition of the circulatory system.

The present invention provides means whereby fluid flow in vivo may be readily determined and in general, the invention comprises one or more fiber optic differential fluid-pressure measuring devices each having a common optical fiber sensor connected thereto and means for positioning the optical fiber sensor in the flow path at the measurement point. If the devices further consist of several optical fiber sensors, each includes a means for positioning the sensor relative to the measuring position and to each other. In each case, a means for forming a fixed or variable constriction in the flow path of the fluid may be employed. Means are associated with the constriction for positioning the associated optical fiber sensor in the flow path of the fluid at the constriction. The device further includes a fiber optic divided interferometer with means connecting each of the optical fiber sensors in a leg of the divided interferometer. Radiant energy is directed through each of the sensors; and radiant energy detecting means are connected to the divided interferometers. The fiber optic probe described may be used in a wide range of veins and arteries (large and small). One specific example chosen for illustration will be the measurement of total cardiac output.

BRIEF DESCRIPTION OF THE DRAWINGS

The invention will be more particularly described in reference to the accompanying drawings wherein:

FIG. 7A schematically illustrates an alternative technique for reducing optical feedback in a laser-supplied interferometer;

CHARACTERISTICS OF PULSATILE FLOW

Figure 1:
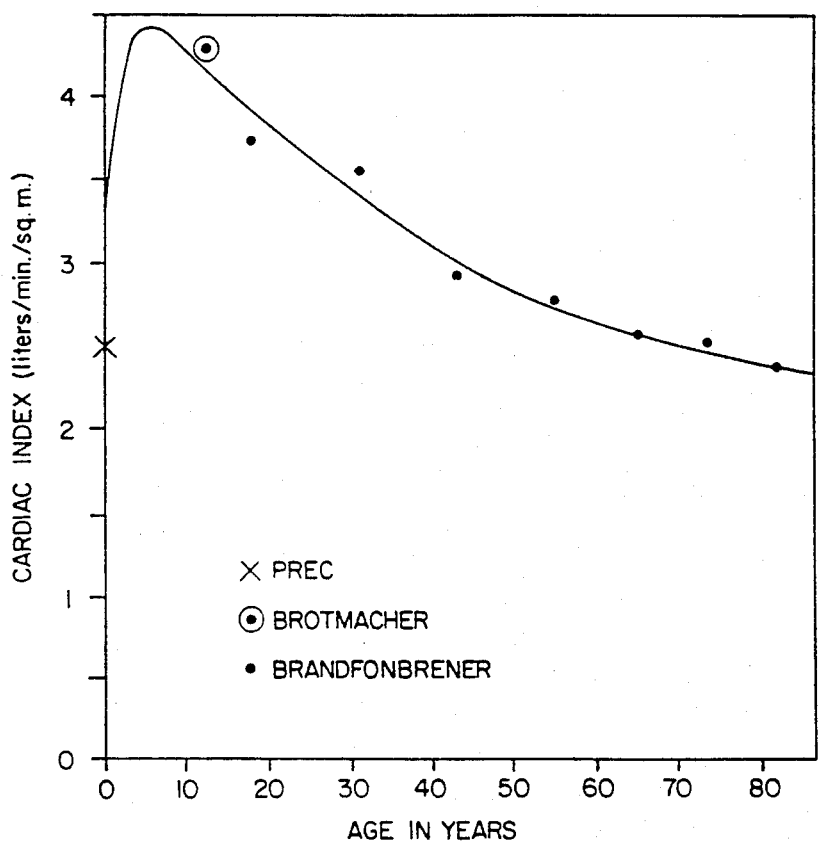
FIG. 1 is a chart illustrating cardiac indices at different ages of a human being.

The cardiovascular system consists of the heart, arteries, capillaries, and veins. All metabolic processes begin and end in this system. These include the exchange of gases in the lungs and in the tissues, the intake of food from the gastrointestinal tract and distribution throughout the body, the transport of nongaseous metabolites from the tissues for elimination in the kidneys, and the dissipation of heat through the lungs and body surface. One of the most important parameters for judging the proper functioning of this system is the quantity of blood transported per unit time (the cardiac output). The output of the ventricles for an adult is approximately 70 ml per pulse and the average pulse rate is 72 beats/min. Thus, the average adult cardiac output is 5040 ml/min. This output may increase significantly upon demand. In the case of athletes during intense exercise, the cardiac output can rise as high as 35 l/min. The specific cardiac output varies with age, sex and body size. The cardiac index is defined as the cardiac output per $m^2$ of surface area. For a normal human being weighing 70 kg, the surface area is approximately 1.7 $m^2$. The cardiac index is shown in FIG. 1 as a function of age. A reduction of the cardiac index to approximately 1.5 (corresponding to 2.5 l/min.) will lead to cardiac shock. About 10% of the patients who experience severe acute myocarditis infarction cardiac shock will die.

Figure 2:
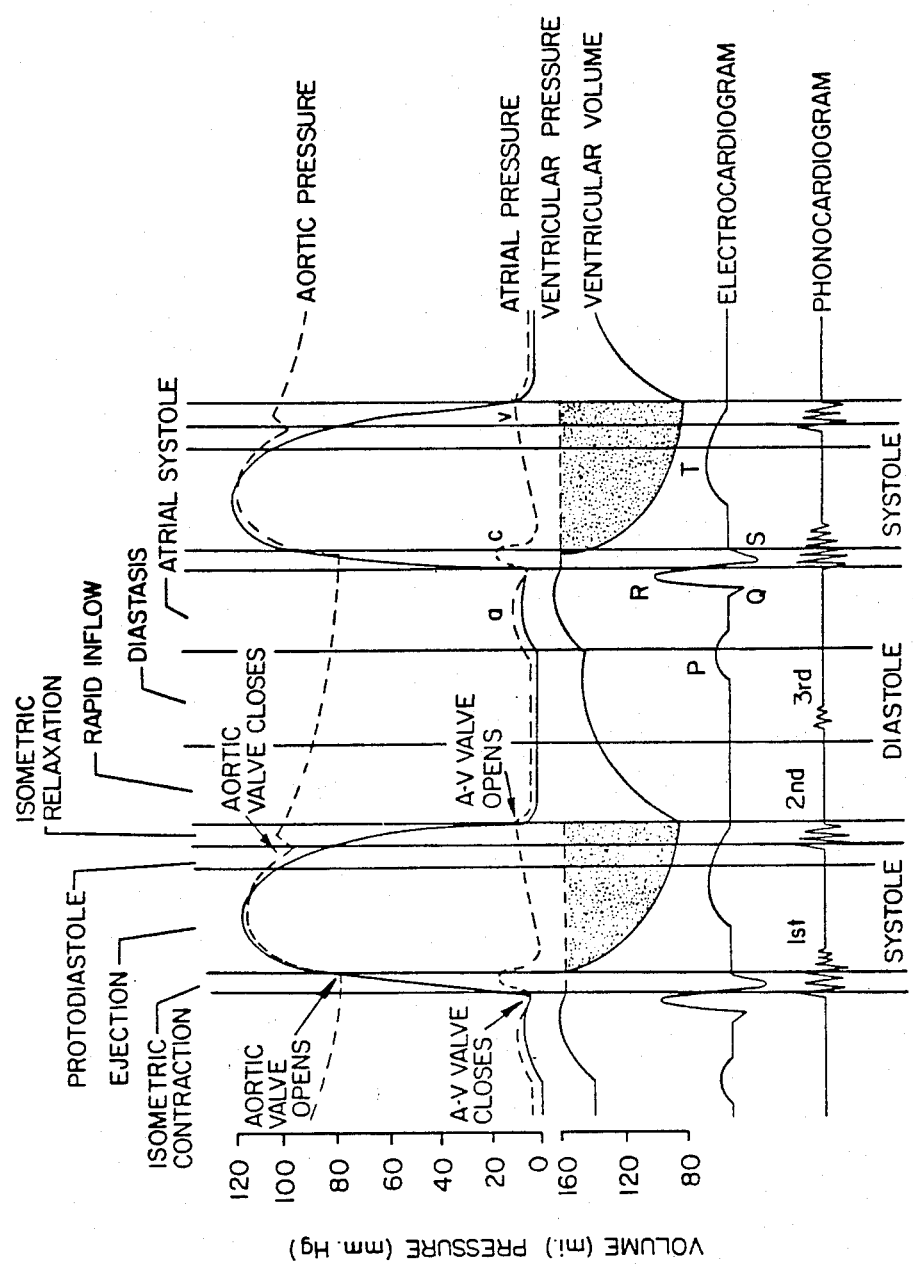
FIG. 2 is a chart illustrating events of a cardiac cycle showing changes in the left arterial pressure, left ventricular pressure, aortic pressure, ventricular volume, the electrocardiogram and the phonocardiogram.

The various events which occur during the cardiac cycle are shown in FIG. 2. The upper three curves illustrate the aortic, atrial, and ventricular pressures, respectively. The fourth curve from the top shows the ventricular volume and the lower two curves are typical traces from an electrocardiogram and a phonocardiogram. Referring to the electrocardiogram, the QRS wave indicates the onset of ventricular contraction. This causes the ventricular pressure to rise and the blood contained to be pumped out as evidenced by the decrease in ventricular volume. The ventricular contraction ends just after the T wave in the electrocardiogram trace. At that time, the ventricle begins to be refilled by the left atrium. Blood is pumped into the main pulmonary artery during the time the ventricle is contracting. The area above the ventricular volume curve during contraction, shown shaded, corresponds to the volume of blood ejected from the ventricle during a single pulse. The derivative of this portion of the ventricular volume curve corresponds to the time rate of change of flow volume. At the point nearest the ventricle, the actual pulse width of the ejected pulse is approximately 1/5 the pulse period, thus, the average pulse height is approximately 25 l/min.

CHARACTERISTICS OF THE ARTERIAL SYSTEM

The total cross-sectional area, blood velocity, and pressure of the main pulmonary artery, aorta, arteries, arterioles, and capillaries are shown in Table I. The velocity of the pressure pulse is approximately ten times the velocity of the blood flow pulse given in this table. As can be seen, the total cross-sectional area of the capillaries is approximately $10^3$ times that of the main pulmonary artery and the aorta and the blood velocity is approximately $10^{-3}$ that in the main pulmonary artery and the aorta. The aorta itself decreases in diameter with distance from the heart. The taper measured by D. J. Patel in large mongrel dogs corresponded to approximately 3% decrease in cross-sectional area per cm. The ascending aorta and main pulmonary artery are relatively elastic. During the pressure pulse Patel et al. have reported that the ascending aorta and pulmonary artery change their diameters by 6% and 11%, respectively.

TABLE I

| PART | AREA cm$^2$ | VELOCITY cm/sec | PRESSURE mmHg |
|---|---|---|---|
| Main Pulmonary Artery | 6.0 | 30.00 | 20–30 |
| Aorta | 4.5 | 40.00 | 80–120 |
| Arteries | 20.0 | 9.00 | 75–130 |
| Arterioles | 400.0 | 0.45 | 50–90 |
| Capillaries | 4500.0 | 0.04 | 0–30 |

TECHNIQUE FOR FLOW MEASUREMENT

Fluid-flow measurements have a large variety of applications including the measurement of flowing liquids, gases, and slurries for transportation of goods, chemical materials, and vehicle fuel flow. In general, flow sensors consist of a primary element that is in contact with the flowing fluid and a secondary device that measures the action of the fluid stream on the primary element. In the differential pressure technique of the present invention, the primary element is a constriction or section of tube into which is introduced a variation in cross-sectional area. This produces a differential pressure proportional to the flow rate. The secondary element is a differential pressure cell which is the device that measures this differential pressure.

Conventional Techniques for Measuring Cardiac Output

A variety of techniques are presently employed for measuring cardiac output. These include the Fick procedure which involves measuring the ratio of the oxygen absorbed per minute by the lungs to the difference in the oxygen content of the arterial and venous blood. The thermal dilution technique involves injecting a fixed amount of cold solution into the right atrium and measuring the temperature change down stream in a pulmonary artery. The dye dilution method unlike the two above methods, does not involve cardiac catheterization. In this case, a known quantity of dye is injected into a vein and the output of an artery is passed through a photospectrometer which measures the concentration versus time determined. The thermal dilution technique s most often used today. The thermal dilution and an alternate hybrid approach will be discussed in some detail below.

Differential Pressure Technique For Measuring Flow

One method commonly used for determining flow requires the measurement of the differential pressure associated with a change in the cross-sectional area of a flowing liquid. The relevant equation, known as Bernoulli's equation, applies to an incompressible fluid that flows through a tube of varying cross sections. It can be obtained directly from Newton's second law. The Expression can be written in the form $$P_1 + \rho g y_1 + \tfrac{1}{2}\rho V_1^2 = P_2 + \rho g y_2 + \tfrac{1}{2}\rho V_2^2 \qquad (1)$$

The subscripts refer to the two points where the measurements are made. P is the absolute pressure in N/m$^2$, $\rho$ is the density of the fluid in kg/m, g is the gravitational constant, y is the elevation at the location of the measurement, and V is the velocity in m/s. Furthermore, from the equation of continuity $$Q = A_1 V_1 \rho = A_2 V_2 \rho \qquad (2)$$

one obtains $$V_1 = A_2/A_1 V_2 \qquad (3)$$

where Q is the quantity of fluid in kg/s and A is the cross-sectional area in m$^2$. Assuming $y_1 = y_2$ (in the present application where the orientation will be changing due to movements of the patient, a correction for the elevation may be necessary but for this analysis, will be ignored), and solving for
$P_{12} = P_1 - P_2$ from Eqs. (1), (2) and (3) yields
$$P_{12} = (Q^2/2\rho)(1/A_2^2 - 1/A_1^2) \qquad (4)$$

A square root relation between Q and $P_{12}$ follows from this expression. The units of $P_{12}$ are N/m$^2$ or pa. This can be converted to mm Hg by using the fact that 13.3 pa = 0.1 mm Hg. In the present device, the values of Q expected are from 1.0 l/min to 15 l/min (3.0 x 10$^{-4}$ kg/s to 4.5 x 10$^{-3}$ kg/s). In order to attain 0.5% accuracy at the lower limit, it will be necessary to measure cardiac output over 2 orders of magnitude. This requires that the dynamic range of the pressure measurement be 4 orders of magnitude. Conventional catheter pressure measuring devices fail to satisfy this requirement by at least 1 order of magnitude. The fiber optic sensors of the invention exhibit the required dynamic range.

Eq. (4) can be solved for Q in terms of the differential pressure and the cross-sectional areas. However, in order to determine the cross-sectional areas. However, the inside dimensions of the artery must be known. If the artery being measured has a constant cross-sectional area, then the differential pressure can be measured at two adjacent positions and the cross-sectional area of the artery, as well as Q, can be determined.

Two differential pressure measurements $P_{12}$ and $P_{13}$ expressed by equations in the form of Eq. (4) are made. The ratio of these expressions is given by Eq. (5) where Q has been cancelled:

$$P_{12}/P_{13} = (1/A_2^2 - 1/A_1^2)/(1/A_3^2 - 1/A_1^2) \quad (5)$$

where $A_1$, $A_2$ and $A_3$ can be expressed in terms of the unknown radius of the artery and the radius of the respective probes in the form $$A_i = \pi r_a^2 - \pi \delta_i^2 r_a^2 = \pi r_a^2 (1 - \delta_i^2) \quad (6)$$

and $r_i = \delta_i r_a$ is the radius of the ith probe. The relation between the values of the various i's are known for the individual probes, thus letting $$\delta_i = \delta, \ \delta_2 = a\delta, \ \delta_3 = b\delta \quad (7)$$

where a and be are known. Substituting Eq. (6) and Eq. (7) into Eq. (5) yields $$P_{12}/P_{13} = [1/(1-a^2\delta^2)^2 - 1/1-\delta^2)^2]/[1/1-b^2\delta^2)^2 - 1/(1-\delta^2)^2] \quad (8)$$

After some algebraic manipulation it can be shown that Eq. (8)

$$P_{12}/P_{13} = \frac{[[(1-a^4)\delta^2 + 2(a^2-1)](1-b^2\delta^2)^2]}{[[(1-b^4)\delta^2 + 2(b^2-1)](1-a^2\delta^2)^2]} \quad (9)$$

which is a cubic equation in $\delta^2$, having at least one real root. Thus, using the measured values of $P_{12}$ and $P_{13}$, $\delta$ can be calculated and used in Eqs. (7) and (6) to obtain the values of $A_1^2$ and $A_2^2$ required in Eq. (4). Thus, with two differential pressure measurements the diameter of and flow through a tube can be continuously monitored.

Alternate techniques of directly measuring the inside dimensions of the artery by an independent technique may be used. These include thermal and dye dilution, ultrasonics, x-rays, etc. In this case only, one differential pressure measurement would be required.

Consideration must be given to measurements made in a tapered region of an artery. In this case, the probes can all be of equal diameter. The differential pressures will be produced as a result of the naturally occurring taper. At the upstream location (i.e., nearest to the ventricle), a variable probe diameter will permit the taper to be measured. This can be accomplished by expanding the diameter of the probe until the value of $P_{12}$ measured between the first two sensing regions is zero and repeating the process until the value of $P_{13}$ between the first and third locations is reduced to zero. The values of Q and the arterial dimensions can then be determined as a function of time from the subsequent measurements of $P_{12}$ and $P_{13}$. In addition to the rate of flow and the dimensions of the vein or artery, the elastic coefficients of the vessel walls can also be determined. This coefficient can be defined by the relation $$E_p = R \ \Delta P / \Delta R \quad (10)$$

where R is the mean radius, $\Delta P$ is the pulse pressure, and $\Delta R$ is the change in radius during the cardiac cycle. Values of $E_p$ reported by Patel et al. For various blood vessels are given in Table II.

TABLE II

| Blood Vessel | $E_p(g/cm^2)$ |
|---|---|
| Main Pulmonary Artery | 163 |
| Ascending Aorta | 779 |
| Femoral Artery | 4414 |
| Carotoid Artery | 6197 |

The vessels become stiffer (larger $E_p$) with distance from the heart. The value of $E_p$ for the main pulmonary artery is significantly less than that of the ascending aorta except in the case of patients exhibiting pulmonary hypertension. Patel et al. reported on three such patients where the value of $E_p$ corresponding to the main pulmonary artery was observed to be approximately five times the corresponding value given in Table II. Finally the presence and location of stenosis can be determined by the use of such a sensor.

FIBER OPTIC SENSORS

Fiber optic differential pressure sensors have the advantages of no moving parts, applicable to the measurement of flow in most fluids, and well-established performance; however, because of their great sensitivity and large dynamic range, they do not suffer from the disadvantages of conventional differential pressure cells (i.e., limited usable flow range due to the square root relation between flow and differential pressure shown in Eq. (4) and an unrecoverable pressure drop). Thus, both the variation in cross-sectional area introduced by the constriction and the resulting unrecoverable pressure drop may be minimized due to the great sensitivity of fiber optic sensors. Furthermore, the large dynamic range yields a wide usable flow range (>3 orders of magnitude). In addition, fiber optic differential pressure sensors have a number of additional features such as immunity to EMI (electromagnetic interference), ability to operate at high temperatures, small size, high reliability, and low power operation.

A fiber optic pressure sensor consists of at least one optical fiber and a means for enabling the pressure to modulate some property (i.e., phase, intensity, polarization, color, etc.) of the light in the optical fiber. The system consists of a source, one or more photodetectors, a means of demodulating the signal, and various other optical components such as fiber stretchers, fiber deformers, couplers, connectors, mirrors, and means for inserting light from the source into the optical fiber with a minimum of light reflected back into the source. In addition, a means for changing the diameter of the probe and/or to measure the diameter of the veins or arteries may be included.

Figure 3:
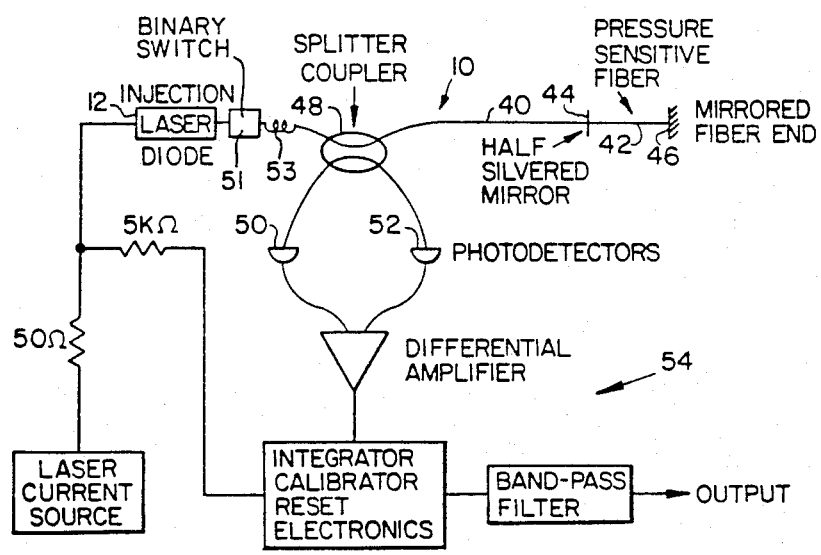
FIG. 3 is a schematic showing of a fiber optic Fabry-Perot interferometer and associated electronics for a pressure measuring device.
Figure 11:
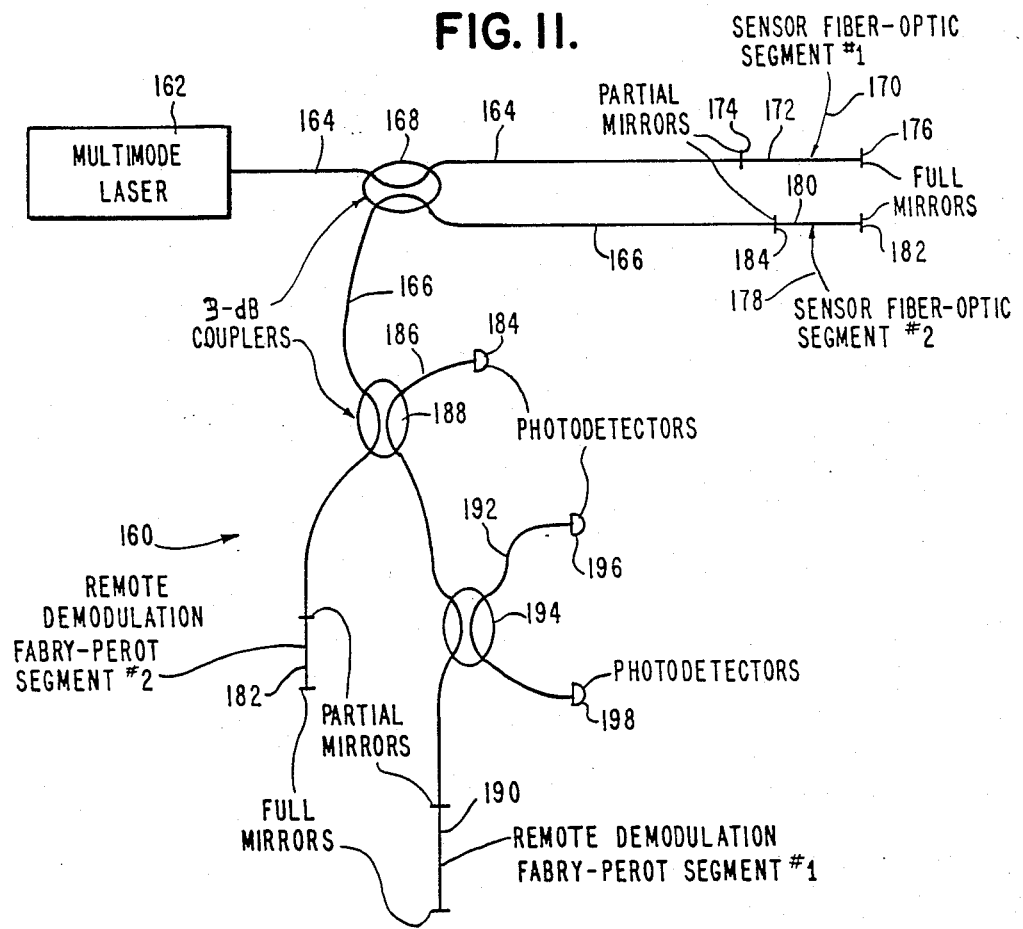
FIG. 11 illustrates a divided Fabry-Perot interferometer useful with the structures shown in FIG. 10.

The Fabry-Perot interferometer 10, shown schematically in FIG. 3, differs from other interferometers in that the two arms of the interferometer are combined in the same optical fiber 40. Thus, only a single pressure may be measured with the configurations shown in FIG. 3. (FIG. 11 illustrates a configuration where two sensors are employed.) In FIG. 3 light from the laser 12 is beam split at the splitter/coupler 48, one part into the fiber 40 and the other portion going to the photodetector 52. At the end of optical fiber 40 is a pressure sensitive region 42 separated from the remainder of the optical fiber by a half-silvered mirror 44. The other end of the pressure-sensitive region is fully mirrored as at 46. Thus, light is divided by the half-silvered mirror, one part being reflected back toward the coupler/splitter 48 and the other part being transmitted into the optical-fiber portion 42. The latter part of the light is phase modulated, reflected by the full mirror 46 at the end, and interferometrical recombined at the half-silvered mirror 44 with the part of the light that is not transmitted through the half-silvered mirror. Part of the light in the region 42 may be reflected back and forth between the two mirrors 44 and 46 before being transmitted back through the half-silvered mirror 44. Each time the light passes through the region 42, the phase modulation is increased. The coherence length of the light in the fiber must be greater than twice the length of the region 42. The intensity-modulated light propagates back along the fiber to the coupler/splitter 48 where it is divided, one portion going to the photodiode 50 and another portion going toward the laser 12. The part of this latter portion of light which gets back into the laser must be minimized. The outputs of the two photodetectors 50 and 52 are combined in the demodulation/signal-processing circuitry 54.

Figure 4A:
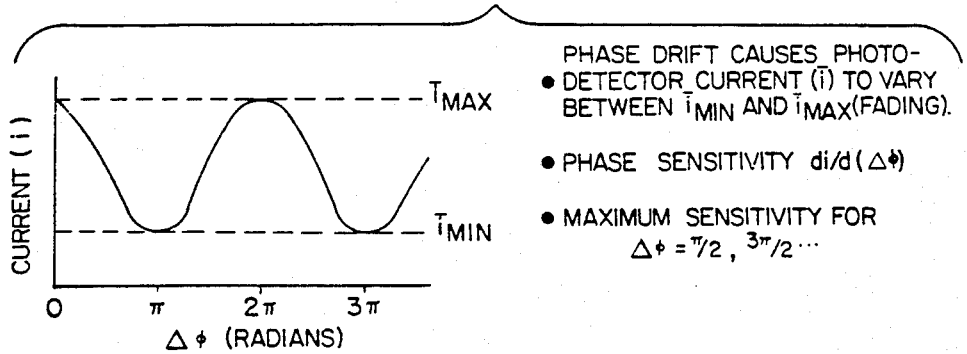
FIG. 4A graphically illustrates the photo detector output current resulting from light wave phase-change fiber optic sensor output.

If the outputs of the arms of the interferometer are initially in phase, they will interfere constructively when recombined. If the difference in phase, $\Delta\phi$, between the arms of the interferometer increases because of a pressure fluctuation, the amplitude of the output signal from both photodetectors 50 and 52 decreases, reaching a minimum when $\Delta\phi=\lambda/2$ (i.e., $\pi$ radians). If the value of $\Delta\phi$ continues to increase, the output amplitude will increase, returning to its maximum value when $\Delta\phi$ becomes $2\pi$. The electrical current out of one of the photodetectors 50 or 52 caused by the optical signal is shown in FIG. 4A. The outputs of the two photodetectors 50 and 52 are combined in a differential amplifier 64 FIG. 5. Since the amplitude modulations of the current from the two photodetectors are 180° out of phase, combination in the differential amplifier rejects common-mode amplitude fluctuations. By carefully matching the lengths of fiber in the interferometer arms laser phase noise can be reduced by five to six orders of magnitude. In this manner, values of $\Delta\phi$ of $10^{-5}$ radians and below can be detected at low frequency (i.e., ~1 Hz).

Figure 4B:
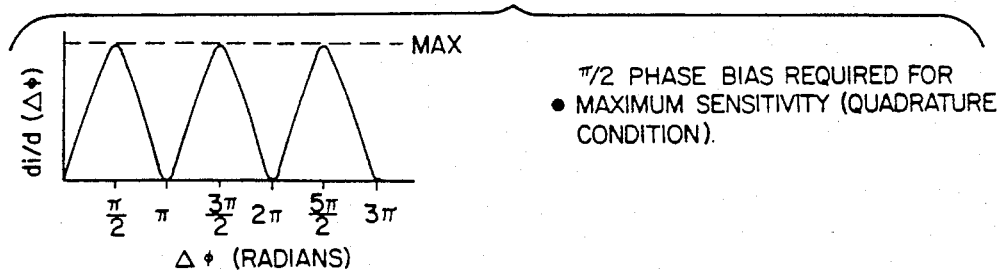
FIG. 4B graphically illustrates the derivative of the photo detector output current resulting from light wave phase-change fiber optic sensor output.
Figure 6:
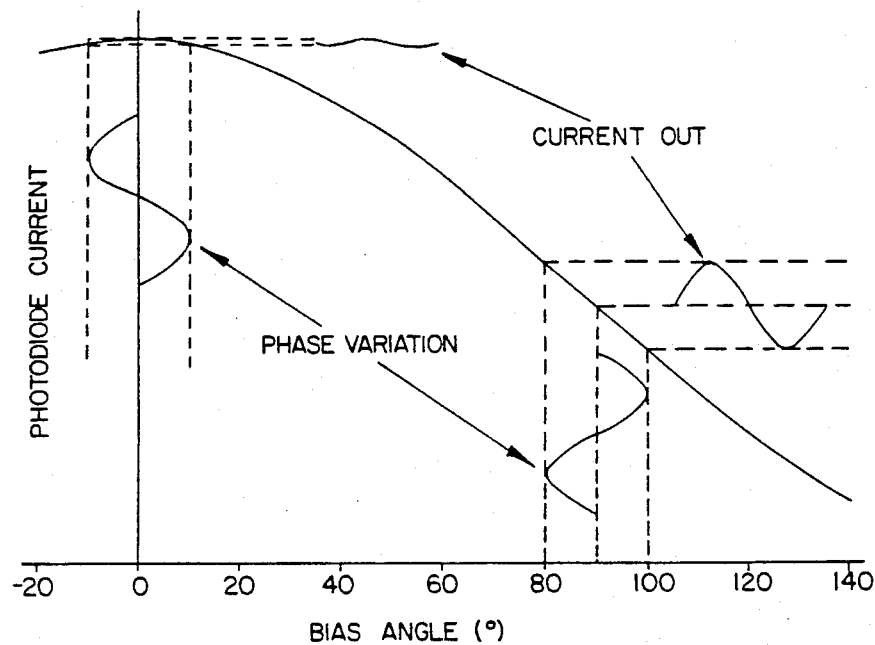
FIG. 6 graphically illustrates the sensitivity of fiber optic homodyne sensor at 0 and 90 bias angle.

The feedback circuit also ensures that the interferometer is operated in its most sensitive mode. Any large amplitude drift (change) greatly increases the difficulty of measuring small changes. The signal to be considered will appear as a small amplitude perturbation on the photodetector current, as shown in FIG. 6. The sensitivity to phase changes varies as the slope of the photodetector curve. Thus, the curve of FIG. 4B, obtained by taking the derivative of the photodetector output with respect to $\phi$, is the phase sensitivity for small amplitude changes. The maximum sensitivity occurs for odd multiples of $\pi/2$, while zero sensitivity occurs for even multiples $\pi/2$. This is shown in FIG. 6. Here the photodiode current is plotted against the bias (phase) angle. In order to demonstrate the sensitivity, a cw (sinusoidal) signal of amplitude 10 (electrical degrees) is shown superimposed on a bias (quiescent or operating value of the relative phase) point 0° and at 90°. The amplitude of the resulting output current is obtained by projecting the phase oscillation (input signal) upward onto the solid curve graphically and plotting the resulting output current along a horizontal line, as is normally done graphically with any transfer function. At 90° bias, the resulting current is large and of the same frequency as the input signal. At 0° bias, however, the amplitude of the photodetector current is small and exhibits a frequency that is twice the excitation frequency because the oscillation extends on both sides of the maximum.

Figure 5:
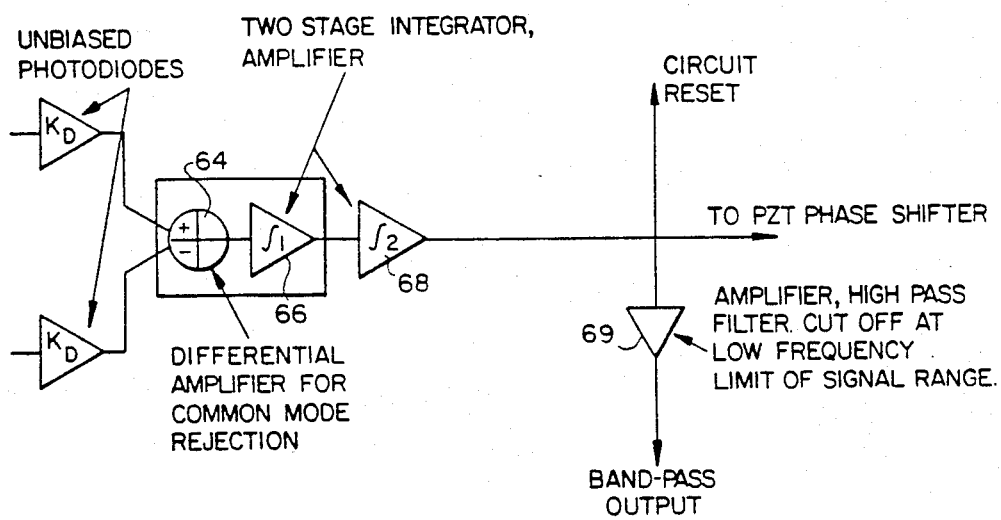
FIG. 5 schematically illustrates a phase-locked-loop homodyne detection circuit.
Figure 5A:
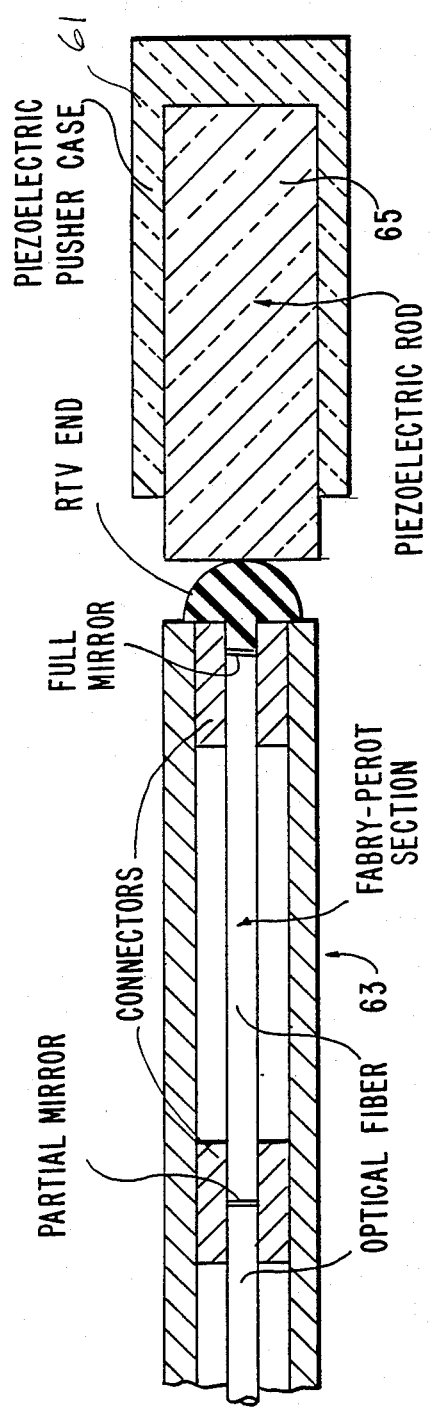
FIG. 5a illustrates a remote Fabry-Perot cell with a piezoelectric rod for phase-locked-loop feedback.

Returning to FIG. 5, the output of the differential amplifier 64 is integrated to eliminate drift and is fed back to the P&T pusher FIG. 5a located in the demodulation branch, to compensate for the phase shift in the sensor branch is to lock the relative phase at the point of maximum sensitivity.

Two photodetectors are shown in FIG. 3. The photodetectors are operated in an unbiased condition in order to eliminate dark current noise. Their outputs are combined in the differential amplifier 64 that provides common-mode rejection as well as amplification. This is followed by one or more stages of integration at 66 and 68 and, possibly, additional amplification. These two integrator amplifiers 66 and 68 pass all signals from DC up to the highest frequency of interest. The output of the two-stage integrator amplifier is used to phase lock the arms of the interferometer. The effect is to produce a phase change in the interferometer arms equal to that caused by the signal being detected. In addition, the interferometer is maintained in quadrature, i.e., is phase locked. If the phase were exactly locked, there would be no output signals from the interferometer. Therefore, there must be an error signal at the photodetectors in order to have a feedback signal. The feedback circuit thus amplifies the error signal from the interferometer and feeds it back to a piezoelectric pusher 61 acting on the remote Fabry-Perot cell 63 (See FIG. 5a). The voltage applied to piezoelectric rod 65 increases until phase change in the Fabry-Perot optical fiber section is equal to that produced by the differential pressure acting on the sensor Fabry-Perot optical fiber section. In this manner the interferometer is phase-locked. The feedback voltage required to look the interferometer is directly proportional to the differential pressure being measured. In addition to establishing quadrature, the feedback circuit increases the dynamic range to as much as eight orders of magnitude.

The signal out of the compensating circuit is also fed through a filter 69 that passes the frequency band of interest. This constitutes the output of the interferometric sensor.

In the feedback schematic shown in FIG. 5, operational amplifiers (OPAMPS) are used and combined metal oxide semiconductor (CMOS) components are used in the reset circuit. The levels of voltage that can be applied by these circuits to the phase shifter are on the order of 10 volts. The reset circuit tracks the voltage applied to the laser (or phase shifter) and if the limit of the circuit begins to be reached, the phase shifter is rapidly reset to the initial condition and the tracking process begins again. The phase change associated with a large-amplitude, slow drift is compensated for by a number of saw-toothed-like small amplitude phase changes. Care must be taken to minimize the noise during the reset process. In a thermally stable environment, it is common for reset not to occur.

Optical Feedback to Diode Lasers

The effects of optical feedback into injection diode lasers include satellite modes, mode hopping, and multimode operation. The effect of satellite modes can be eliminated by matching the lengths of fiber in the two arms of the interferometer. Mode hopping and multimode operation can be eliminated only by reducing reflections back into the interferometer to 0.1% or less.

Figure 7:
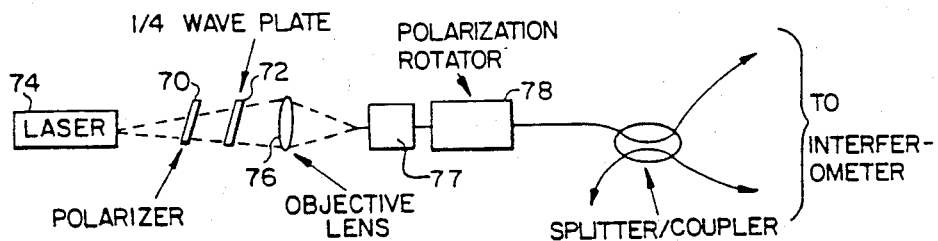
FIG. 7 schematically illustrates one technique for reducing optical feedback in a laser-supplied interferometer.

A significant reduction in light back out of the interferometer into the laser can be achieved by 20 the technique shown in FIG. 7. In this case a polarizer 70 and a ¼ wave plate 72 are located between the laser 74 and the objective lens 76. Each of these devices is oriented at a slight angle ($\sim 12°$) in order to eliminate back reflections. In addition, a fiber optic polarization rotator 78, located in the input fiber 80, allows a twist to be applied to the fiber, thus rotating the direction of polarization. The output of the single-mode injection laser diode 74 is approximately 95% polarized; therefore, by properly orienting the polarization rotator 78, the output can be polarized with very little optical loss. The ¼ wave plate 72 rotates the direction of polarization by 45°. Light reflected from surfaces, such as the objective lens 76, and passing back through the ¼ wave plate have their direction of polarization rotated by an additional 45°. The net result is a 90° rotation in the direction of polarization relative to the orientation of the polarizer. Such back reflected light is blocked by the polarizer 70. The fiber optic polarization rotator 78 is adjusted such that the direction of polarization along which that component of light is oriented, exits from the fiber with an orientation, relative to the ¼ wave plate and polarizer, preventing that fraction of light from reentering the laser. The use of cleaved-cavity injection laser diode may significantly improve the results achieved with this approach. This is due to the fact that these lasers are much less susceptible to mode hopping.

Referring to FIG. 7, still another arrangement involves placing an electro optic modulator 77 between the laser and the input fiber to cut the light on and off without modulating the laser itself. The electro optic modulator can be constructed on an integrated optic chip or can be in the form of a bulk optical component. Another form of electro optic device is a binary switch 51 (see FIG. 3). When the switch is on the incident beam from the laser is introduced to the input waveguide and coupled into the interferometer waveguide which is connected to the interferometer. A length of fiber 53 is again provided as a delay. The light reflected from the mirrors arrives back at the binary switch when it is off. This returning light is not coupled to the input waveguide therefore missing the laser.

The approach chosen to eliminate mode hopping employ a multimode laser source. Since all modes are excited, mode hopping is eliminated. Multimode diode lasers have a significantly shorter coherence length than single-mode diode lasers (e.g. 200 microns compared to as much as 1 meter). The coherence length is the difference in optical path that results in a decrease in interference amplitude by a factor of 1/e. The round trip path length in the Fabry-Perot cell employed as the senior is significantly longer (2.5 cm compared to 0.02 cm). Thus interference does not occur at the partial mirror in FIG. 8 between the light reflected and that making one or more round trips through the sensor Fabry-Perot optical fiber. The remote Fabry-Perot optical fiber is wed to match these path lengths (see FIG. 7a). Light leaves the multimode diode laser 400 and enters the optical fiber pigtailed to it 410. The 3-dB C/S 420 divides the light between the optical fiber dump 440 and the sensor optical fiber 430 The partial mirror 450 reflects a fraction of the light $I_{REF}$. The remainder of the light $I_{SEN}$ travels through the Fabry Perot sensor cell 470, reflects off the full mirror 460 and retrace its path through the sensor cell 470 and is recombined at the partial mirror 450 with the reference light $I_{REF}$. A portion of the $I_{SEN}$ light makes several passes through the Fabry-Perot sensor cell before recombining with $I_{REF}$ light. The recombined light returns through 430 to the 3-dB C/S 420 where it is split, half passing through the lead optical fiber 410 to the laser 400. Since the laser is already operating multimode the light reflected back to the laser does not cause mode hopping. The other half of the reflected light is coupled into optical fiber 480 propagates to the 3-dB C/S 490 that divides half to the photodetector 520 and the other half to the partial mirror 560. Again part is reflected and part transmitted into the remote Fabry-Perot cell 500. The latter part reflects at the full mirror 570 and returns its path to the partial mirror 560 where it recombines with the reflected light. That portion of $I_{REF}$ that makes a double path pass through the remote Fabry-Perot interferes with that portion of $I_{SEN}$ that reflects at the partial mirror 560. The resulting interference produces an amplitude modulated portion a part of which is coupled by the 3-dB C/S into the photodetector 510.

Interferometric Sensor Probes

Two techniques for the fabrication of probes that exhibit sufficient sensitivity for the present application will be described below. The required sensitivity calls for a minimum detectable pressure of 0.1 mm Hg (13.3 N/m$^2$) and a dynamic range of 4 orders of magnitude. Furthermore, the probe size must be compatible with catheter dimensions. A probe with a diameter and length of approximately <5 mm and 1 cm, respectively, would be satisfactory. The frequency range of interest for medical applications is from 0.5 Hz to 500 Hz. For other applications, it will be higher.

Transduction Mechanism Due To Pressure Induced Length Changes

The transduction mechanism by which hydrostatic pressure induced length changes produces a phase change in the optical path length is discussed below. The phase $\Phi$ can be expressed in terms of the refractive index n, the fiber length, L, and the wave number, k, by the equation $$\Phi = knL$$

where $k = 2\pi/\lambda o$ and $\lambda o$ is the wavelength of light in vacuum. Changes in k, n, and L result in changes in $\Phi$. The corresponding expression relating these changes is;

$$\Delta\phi = k\Delta(nL) = knL \ (\Delta n/n + \Delta L/L)$$

where $\Delta L/L$ is the axial strain, $S_{11}$, and $\Delta n$ is given by
$$\Delta n = ((n^3/2)[(P_{11}+P_{12})S_{12}+P_{12}S_{11}])$$

where $P_{11}$ and $P_{12}$ are the Pockel's coefficients and $S_{12}$ is the radial strain. For changes occurring at constant volume $S_{12} = -S_{11}/2$. This expression assumes a value of 0.5 for Poissons ratio. This assumption is valid for the jacket and mandrel materials which will be used since their Poissons ratios approach 0.5 (e.g., in Hytrel ™ the value of the Poissons ratio is 0.483). Combining Eqs. (12) and (13) and expressing $S_{12}$ in terms of $S_{11}$ yields $$\Delta\phi = knL (1 + n^2(P_{11} - P_{12})/4)S_{11}$$

The strain $S_{11}$ can be applied in a variety of ways, two of which are the use of specialized materials as the fiber jacket or as a mandrel on which the fiber is wound. The former approach will be used for the present application. In fused silica, $P_{11} = 0.12$, $P_{12} = 0.27$ and $n = 1.46$. Substituting into Eq. (14) becomes $$\Delta\phi = 0.92 \, kLnS_{11}$$

The $\Delta n/n$ term in Eq. (12) affects the value of $\Delta\phi$ by only 8% (i.e., if $\Delta n/n$ were neglected in Eq. (12), then $\Delta\phi = knLS_{11}$ would result). The value of $S_{11}$ depends upon the configuration of the optical fiber and the manner in which the stresses are applied. If the fiber has a thick jacket, the value of $S_{11}$ will be dominated by the jacket material. For an isotropic material subjected to hydrostatic pressure, $$\Delta L/L = \Delta V/3V \simeq (1/3V)(\delta V/\delta P)\Delta P$$

where V is the volume, P is the hydrostatic pressure, and $(1/V)(\delta V/\delta P)$ is the compressibility, K. Thus, Eq. (16) becomes $$\Delta\phi = 0.31 \, kLnK\Delta P$$

This expression is valid for the thick coating case where the pressure sensitivity is determined by the fiber jacket alone. For thinner jackets, $S_{11}$ is not a function of the jacket compressibility alone. For jackets of finite thickness, to first approximation, the value of $S_{11}$ is governed by an effective Young's modulus, defined as the cross-section area average of the Young's modulus of the glass and of the jacket material. The maximum value of $\Delta\phi$ will not exceed the value indicated by Eq. (17) For materials with a large Young's modulus, thick-jacket behavior can be realized with relatively thin jackets. The ideal jacket material will, therefore, have large compressibility and large Young's modulus. Some materials that meet these requirements are Teflon, polypropylene, nylon, and Hytrel. Solving Eq. (17) for the minimum detectable differential pressure, P, in terms of the minimum detectable phase change, yields $$P_{min} = \Delta\phi_{min} [0.31 \, nkKL]^{-1}$$

Letting $\lambda_o = 0.82 \times 10^{-6}$m $K = 2.67 \times 10^{-10}$ m/n (Hytrel), and $n = 1.46$ in Eq. (18), results in $$\Delta P_{min} = 1.08 \times 10^3 \Delta\phi_{min}/L(m)$$

$$\Delta P_{min} = 1.08 \times 10^3 \Delta\phi_{min}/L(m)$$

For $L = 0.01$m and $\Delta\phi_{min} = 10^{-4}$rad, $\Delta P_{min} = 10.8$N/m² $= 10.8$Pa, which satisfies the sensitivity requirement indicated above. The value of $\Delta P_{min}$ is defined as S/N=1 measured in a 1-Hz band. The dynamic range achievable with these probes is 6 orders of magnitude. The results are relatively flat over the frequency range of interest.

THE PRESENT INVENTION

In my prior applications two Optical Fibers were required to measure differential pressure with a single sensor. It has now been discovered that by forming the sensor as part of a Fabry-Perot interferometer only a single optical fiber is required.

Figure 8:
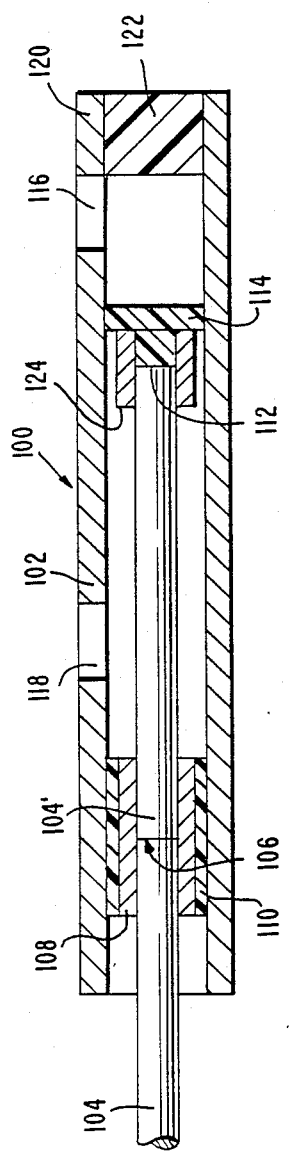
FIG. 8 illustrates a Fabry-Perot differential pressure sensor of the invention employing a single optical fiber.

In its simplest form illustrated in FIG. 8 a differential pressure sensor 100 is illustrated and comprises a capillary tube 102 within which is mounted an optical fiber 104. The optical fiber 104 is provided with a partially silvered mirror 106 at one end and is couple to another segment of the optical fiber 104'. The optical fiber and its segment are connected by a connector 108 and the external surface of the connector is attached to the internal bore of the capillary tube by, for example, an epoxy resin 110. The optical fiber segment 104' terminates with a full mirrored end 112 about which is provided half of a connector 124. An elastomeric piston 114 is attached at the end of the connector 124 filling that portion of the connector not occupied by the fully mirrored end 112 of the optical fiber. On one end of the capillary tube is a first orifice 116 and on the opposite side of the piston 114 is a second orifice 118. The remote end 120 of the capillary tube is sealed with an epoxy, for example, plug 122. Pressure exerted on opposite sides of the piston 114 through the orifices 116 and 118 causes the piston 114 to exert pressure on the optical fiber segment 104'. The difference in pressure results in an axial length change in the fiber, and therefore an optical phase shift in the fiber optic segment 104' which is free to move at the end adjacent to the piston 114 and constrained from movement at its opposite end by the epoxy resin 110.

The piston 114 may comprise a diaphragm which would also apply pressure against the free to move end of the optical fiber segment resulting in an axial strain and therefore an optical phase shift in the fiber optic segment.

Figure 9:
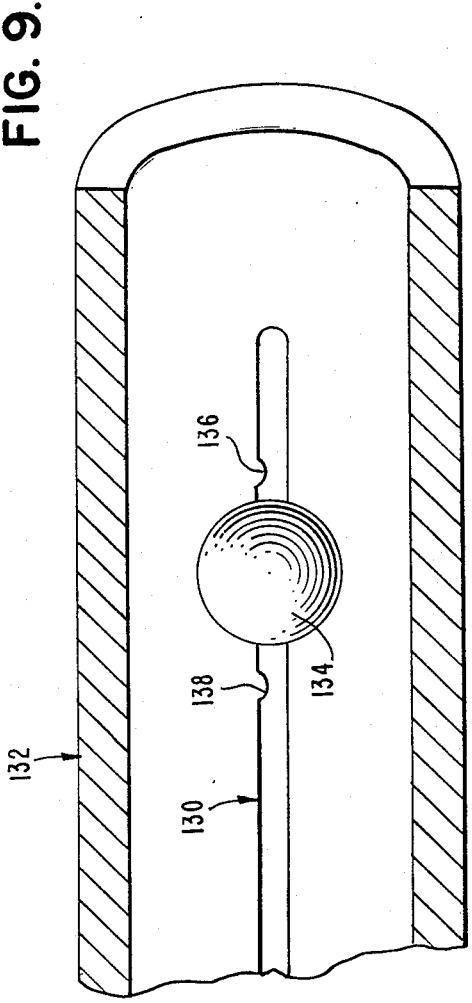
FIG. 9 illustrates the use of an enlarged zone located between a pair of orifices so that pressure difference caused by the enlarged zone is measured with a single fiber.
Figure 10:
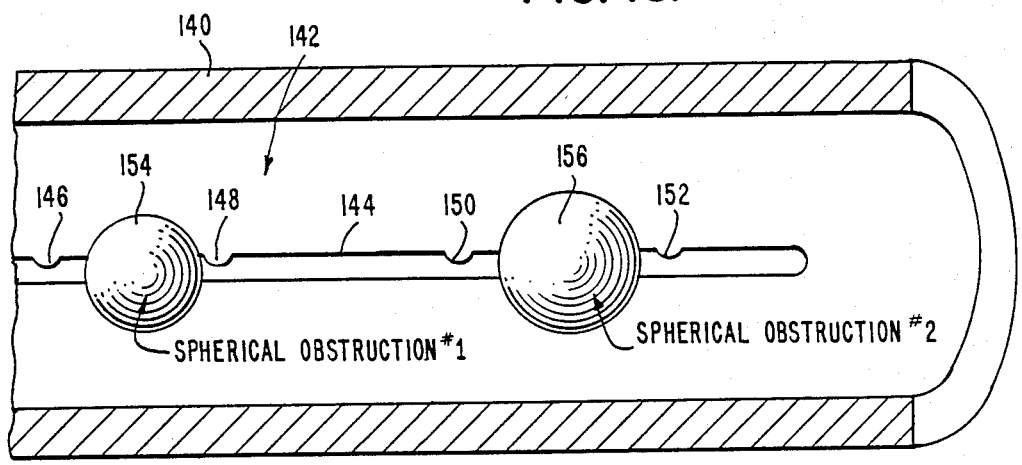
FIG. 10 illustrates simultaneous measurement of pressure differentials caused by two enlarged zones and four pressure orifices.

Diaphragms have been used in the design of pressure sensors employing optical fibers. In such prior art sensors the light was reflected from the diaphragm and the diaphragm did not exert a force on the optical fiber. Thus the separation between the end of the optical fiber and the diaphragm was proportional. In the present case the diaphragm is used to exert a force on the optical fiber segment and is not employed to reflect light. Referring now to FIG. 9 the sensor 130 is illustrated within an artery 132 and an obstruction 134 such that a spherical element is positioned between first orifice 136 and a second orifice 138. The enlarged zone 134 is thus located between the pair of orifices 118 and 116 in FIG. 8 then the pressure difference caused by the enlarged zone is measured with a single fiber. Thus, two fibers of my prior sensors are replaced by a single fiber in the present invention. Likewise, four fibers used to measure the pressure differentials caused by two enlarged zones can be replaced by two fibers. This is illustrated in FIG. 10 wherein the artery 140 has mounted therein fiber optic sensors 142. The capillary tube 144 of the sensors is provided with four orifices 146, 148, 150, and 152. Between orifices pairs 146 and 148 is mounted a spherical obstruction 154 and likewise a second spherical obstruction 156 is mounted between orifices 150 and 152. The utility of the two spherical obstructions form of sensor it diagramatically illustrated in FIG. 11 in which is shown a divided Fabry-Perot interferometer generally designated 160. The system includes a multimode laser 162 which directs light into a single optical fiber 164. The illustration includes a first sensor 170 formed by a first fiber optic segment 172 separated from the optical fiber 164 by a partially, reflecting mirror 174 at the beginning of the segment and a full mirror 176 at the end of the segment. A portion of the light from the laser is coupled to an optical fiber 166 via 3-dB coupler 168. A second sensor 178 formed by a second optic segment 180 separated from the optical fiber 166 by a partially reflecting mirror 184 with a full mirror 82 at the end of the second segment. It will be particularly noted that the first segment 172 has a length greater than the second segment 180 whereby the optic phase shift in the two segments differ. The divided Fabry-Perot Interferometer has a remote demodulation segment 182 equal in length to the second sensor segment 180 which is coupled to photo detector 184 at the end of optical fiber 186 coupled to optical fiber 166 via 3 dB coupler 188. The divided Fabry-Perot interferometer has a second remote demodulation Fabry-Perot segment 190 equal in length to the sensor fiber optic segment 172. The remote demodulation Fabry-Perot segment 190 is coupled to fiber 192 via 3dB coupler 194 and the ends of optical fiber 192 are provided with photodetectors 196 and 198.

The two sensor arrangement illustrated in FIG. 11 can be extended to include N sensors.

CONTINUOUSLY MEASURING CARDIAC OUTPUT

Two approaches for monitoring cardiac output are described. They differ with regard to the measurements required as well as the data they will provide.

The most comprehensive method makes use of two independent P, pressure differential, measurements and eliminates the cross-sectional area of the artery as a variable as this area can be calculated as described herein. This combined with a pressure measurement gives the elasticity of the vein this case, the cross sectional area of the vessel need not be known. A variety of currently used methods would suffice.
 a. Thermal dilution
 b. Dye dilution
 c. Etc.

In the description which follows, the thermal dilution technique will be considered. Once the value of P has been calibrated with an independent flow, measurement (e.g., using thermal dilution), it then is only necessary to monitor the value of P continuously and use it as a measure of flow rate and volume. This measurement will be independent of area or taper of the artery.

Continuous Monitoring of Cardiac Output Using Thermal Dilution for Calibration The major factor determining the quantity of blood puma given time is the quantity of blood which which flows from the veins into the heart during the same time. The blood from the veins is known as the venous return. The peripheral tissue of the body controls its own blood flow. The blood which passes through the peripheral tissue returns by way of the veins to the right atrium. The intrinsic ability of the heart to adapt to widely varying blood input from moment to moment is known as the Frank-Starling law of the heart which may be simply stated: within physiologic limits, the heart pumps all the blood that comes to it without allowing excessive daming of the blood in the veins.

The physiological basis of the Frank-Starling law can be explained as follows:

When an excess (deficit) amount of blood enter the heart chambers, the heart muscles expand further (less). The force of contraction of striated muscles (such as the heart of skeletal muscle) is proportional to their extension (so long as that extension is within physiological limit of those muscles). Thus, the heart contracts with increased (decreased) force automatically pumping the changing amount of blood into the arteries.

A result of the Frank Sterling law of the heart is that the pumping of the heart is almost entirely independent of pressure changes in the aorta. The mean aorta pressure can increase by say 100% above the normal value without significantly reducing the output of the heart. This effect is quite important in that it permits the tissues of the body to control the cardiac output by simply increasing (decreasing) the flow of blood through them. Thus, during exercise when the muscles require increased oxygen, they allow increased blood flow and the heart automatically adjusts to the demand.

Blood flows from the large veins into the right atrium from which it passes into the right ventricle and is pumped into the pulmonary artery. The Swans Ganz catheter is used to measure cardiac output by the thermal dilution technique. The catheter is passed through a large vein, the right atrium, right ventricle, the main pulmonary artery and into a pulmonary artery branch. Quite often, the balloon associated with the Swans Ganz catheter is inflated with air to float the catheter into the position. A pressure sensor at the distal end of the catheter allows the pulmonary wedge pressure to be measured when the balloon is inflated to block the artery. (The wedge pressure measured on the pulmonary arterial side equals the pressure in the pulmonary veins which in turn is approximately equal to the pressure in the left atrium.)

The thermal dilution catheter is equipped with a fluid injectate lumen and thermistors and has its distal end placed in a branch of the pulminary artery. The thermodilution method provides a means of measuring cardiac output by injecting a cold solution into the blood stream such that it is mixed with the blood in heart. The blood in the heart is then pumped past the catheter in the pulmonary artery. The temperature of the blood in the pulmonary artery is measured with a thermistor which records the dilution curve. Cardiac output is calculated by applying equation (20);

$$\text{Cardiac Output} = \frac{V_1(T_B - T_1)C_1C_2}{T_B(t)dt}$$

where $V_1$ is the volume of injectate (typically 10 ml for adults and 2–5 ml for smaller subjects; $T_B$ is the blood temperature; $T_1$ is the injectate temperature. $C_1$ is the density factor which takes into account the difference in specific heats and gravity between the injectate and blood;

$$C_1 = \frac{(\text{Sp. heat})(\text{Sp. gravity}) \text{ injectate}}{(\text{Sp. heat})(\text{Sp. gravity}) \text{ blood}}$$

and $C_2$ is a derived factor which tries to account for the errors inherent in the use of a thermal indicator.

The major factors which affect the accuracy of thermodilution measurements of blood flow are:

(1) Uncertainty of injectate (saline or dextrose) temperature as it passes through the extra-vascular portion of the catheter; namely, the thermal indicator (temperature) is not confined to the blood stream, thus, some indicator is lost to catheter as it moves to the injection port; there is a difference in temperature between the injectate and catheter fluid; and there is a loss of thermal indicator to the surrounding tissue; and (2) for some systems the shape of the dilution curve is not displayed; if so, there could be serious error in measurement due to inadequate injection technique, close proximity of the thermistor to the wall of the pulmonary artery, and uneven respiration and improper placement of the thermistor in the right ventricle or too far distal in the pulmonary artery.

To overcome the disadvantages of the thermodilution technique, OPTECH proposes the measurement of differential fluid pressure inside blood vessels.

Thermal dilution measurements are generally repeated no more often than every few hours. In the interval between measurements, the cardiac output is not measured.

The simplest fiber optic approach of the present invention makes use of a single fiber optic flow sensor behind the balloon (between the balloon and the heart). In this case the arterial dimensions are not measured but instead the process involves calibrating the flow sensor by means of an initial thermal dilution measurement. Subsequently, continuous measurements of P and, therefore, flow will be made. If necessary, the flow sensor may be recalibrated again by means of another thermal dilution measurement. One possible source of error will be the effect of the change in temperature on the P measurement. It may be necessary to collect P data prior to injecting the cold saline solution and then allowing thermal equilibrium to be reached afterward before resuming P measurements. If the Fabry-Perot interferometer is employed, then the sensors also may be used to measure temperature during the thermal dilution process.

ADDITIONAL APPLICATIONS

There are a number of other applications where a small flow sensor may be used and where no existing flow technique will suffice. In the case of a stenosis (a constriction in the artery due to plaque and fatty deposits), the extent of the constriction can be determined by measuring the flow on each side of the stenosis and in the region of the stenosis. Furthermore, if an angioplastic or chemical technique is employed, then such a sensor can be used to determine the success of the procedure. In the latter case, a provision for administering the chemical to dissolve the constriction can be incorporated into the same catheter.

Figure 12:
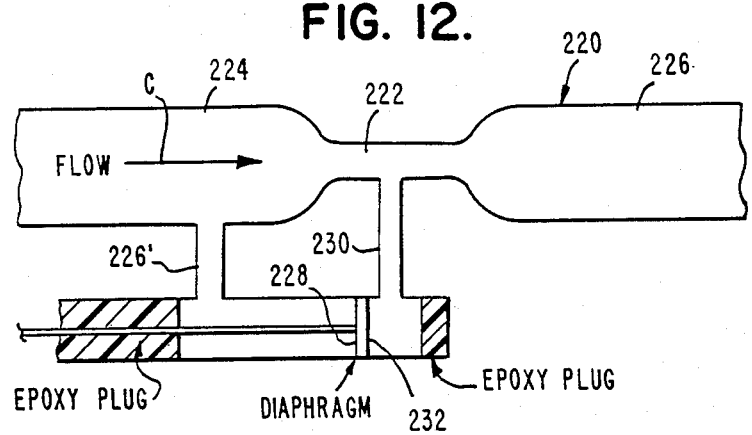
FIG. 12 illustrates diagramatically an industrial application of the present invention.
Figure 14:
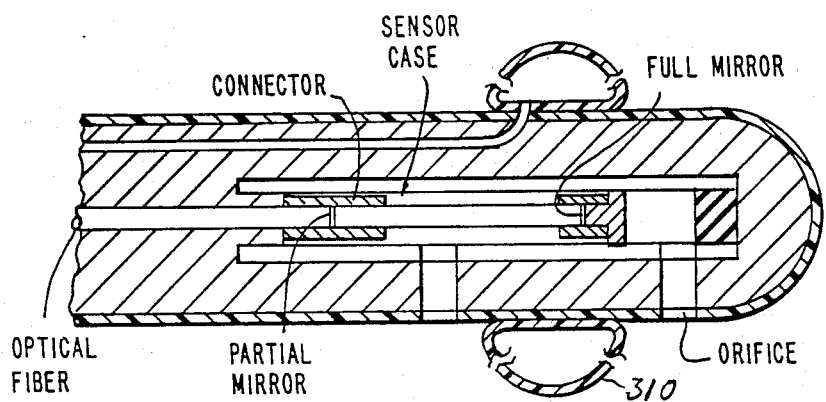
FIG. 14 diagramatically illustrates a variable constriction type fiber-optic flow catheter.

Referring now to FIG. 12 of the drawing, there is illustrated an industrial application of the fluid flow sensing apparatus employing the novel differential optical fiber pressure sensors. In FIG. 12, 220 comprises a conduit having a known area which conducts a fluid flowing in the direction of the flow arrow C. The conduit 220 has a constricted region 222 which changes the pressure/velocity relationship of the fluid in the conduit from that in sections 224 and 226. In section 224, a passage 226' leads to a first sensitive region 228 to sense the pressure of the fluid in section 224, as described in reference to FIG. 9.

In the constricted region 222, the second passage 230 leads to sensitive region 232 to sense the pressure of the fluid in constructed section 222. The output from an opto-electronic demodulator represents the differential pressure in the two regions of the conduit.

Figure 15:
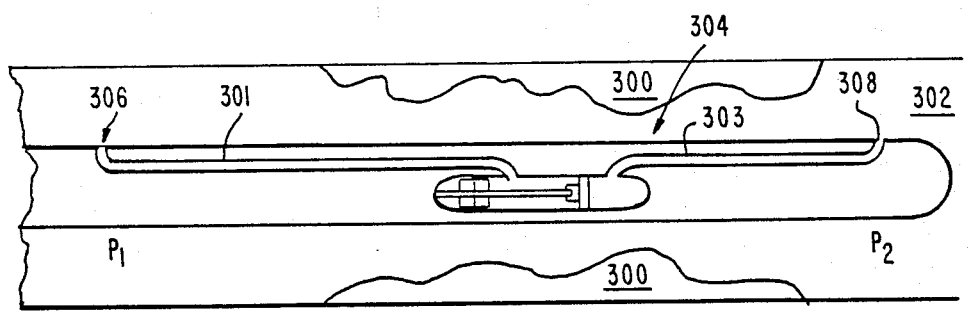
FIG. 15 diagramatically illustrates a fiber-optic catheter designed to measure blood flow past a stenosis.
Figure 13:
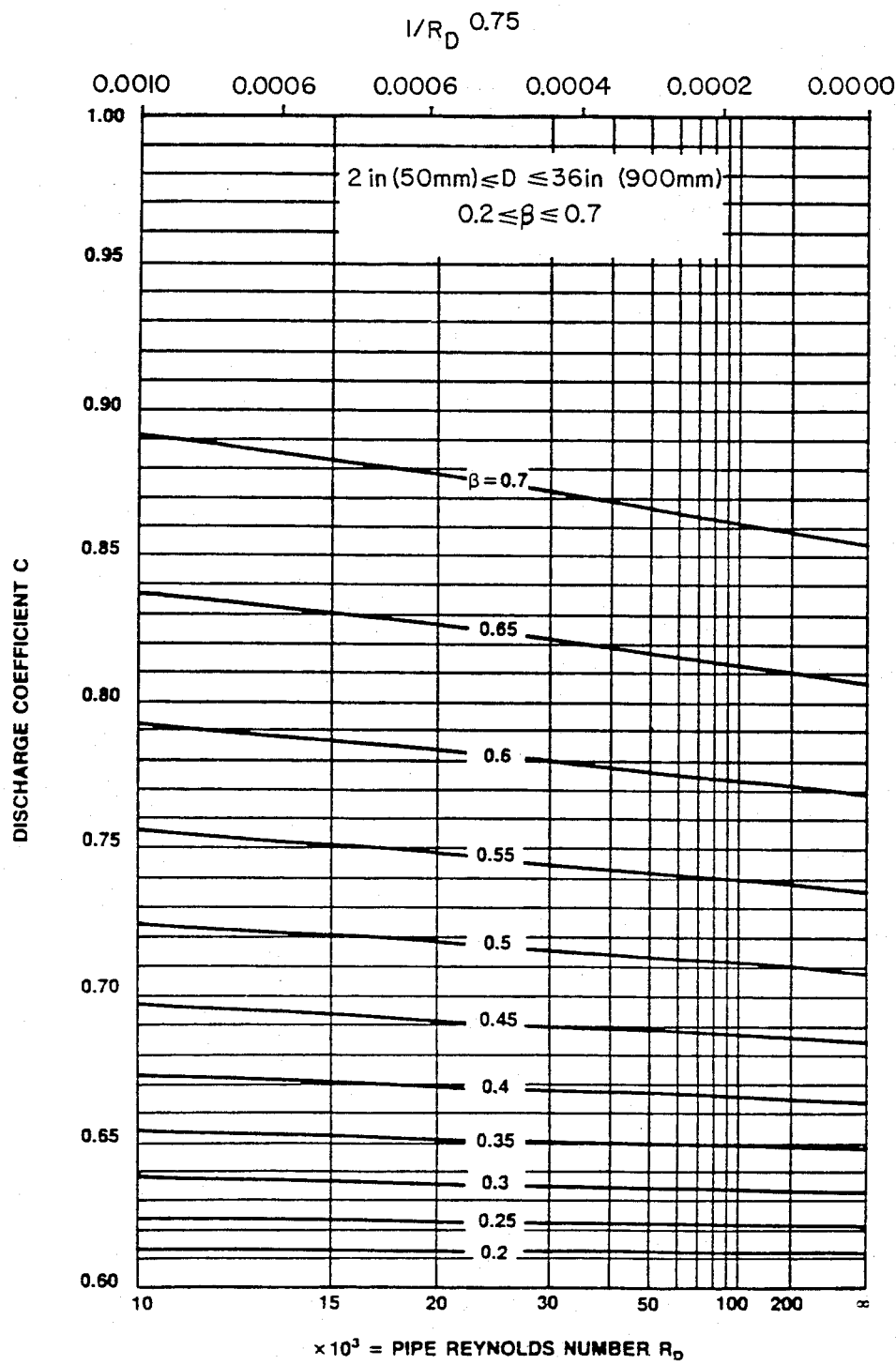
FIG. 13 is a graph showing discharge coefficient C versus the pipe Reynolds number $R_D$ for square edged orifice $2\frac{1}{2}$ D and 8 D pipe taps.

Measuring Flow by Using Fiber Optic Pressure Sensors in a Differential Producer Generating the differential pressure requires that the fluid must go through a change in flow area FIG. 15 as at 300 followed by a return to normal as at 302. The sensor 304 of the invention senses the pressure at 306 and at 308. In the orifice-type flowmeters already in use, this is accomplished by forcing the flow through a small hole with sharp or slightly circular edges upstream and sharp edges downstream. The ratio of the diameter of the hole, d, to the diameter of the normal free area, D, is called $\beta$, the beta ratio.

In this type of device the flow rate is proportional to the square root of the difference between the upstream pressure, $P_1$, and the downstream pressure, $P_2$. Hence, the equation of flow for this geometry is:

$$q = F \sqrt{\frac{h}{pf}}$$

Where:
  q = flow rate
  h = differential static pressure
  ff = density of fluid F is a constant known as the Flow Coefficient. This number adjusts the flow equation for contraction characteristics, pressure measurement locations and velocity profile (Reynolds number); all of which have an effect on the accuracy of the device. The Flow Coefficient also includes an adjustment for the dimensional units used.

$$F = \frac{Cd^2}{\sqrt{1 - B^4}} \cdot K$$

Where:
  d = diameter of obstruction
  B = d/D
  K = adjustment for dimensional units
  C = discharge coefficient All items in F are constant excepting the discharge coefficient, C. This is a dimensionless number which reflects the ratio of the true flow rate to the theoretical flow rate. C comes from the permanent loss of static pressure due to the turbulence from the device itself and is required in all flow meters of this type. It must be determined experimentally.

The diameter of the obstruction can vary from 80% to 25% of D depending on how much accuracy is desired and how much permanent head loss is acceptable. This head loss is dependent on the turbulence created (which increases as the diameter of the orifice decreases), but the sensitivity of the meter is related to the magnitude of the differential.

The flow coefficient usually includes a factor for thermal expansion and gas expansion. These are neglected as they have no real effect in this situation that can be induced (which also increases as the diameter decreases).

Another factor influencing the design of the meter is the orifice diameter's effect on the discharge coefficient over the range of flow rates, FIG. 15 shows this coefficient plotted vs. the Reynolds number. In the ranges considered, it can be seen that while a of 0.7 gives less head loss than a $\beta$ of 0.2, the discharge coefficient remains much more stable at $\beta=0.2$ than at $\beta=0.7$.

The conclusion is that the best design for a differential producer of this type is a balance of desired linearity and acceptable head loss.

It should also be noted that placement of the pressure sensing area inlets for tubes 301 and 303 at $P_1$ and $P_2$ in the meter also has an effect on also has an effect on the accuracy. The largest differential occurs between the free stream pressure taken before the obstruction and the pressure at the vena contracta—the point where the diameter of the coherent jet of fluid coming from the orifice reaches its smallest cross-sectioned area. Since this is the case, measuring the pressures at any other point after the orifice will give a lower differential than is actually occurring. However, any misplacing of these taps will be accounted for in the discharge coefficient and any calibration curve that would be generated for the device.

The pressures are detected by the optical fiber transducers and are resolved by the interferometer. The sensors or transducers will cover a discrete area of the catheter and provide the average pressure in that region. The flow rate is proportional to the square-root of the difference between these two pressures. The equation for the flow rate will be:

$$q = F\sqrt{\Delta h}$$

Where:
g=flow rate in cm$^3$/min
h=head differential detected in mmHg $$F = \left\{ \frac{Cd^2}{\sqrt{\rho\rho(1-B^4)}} \cdot 76.89 \frac{cm^3}{min - mmHg} \right.$$

by the size of blood vessels being examined. FIG. 1 shows an alternative modification to the catheter-probe in which the obstruction consists of an expandable sac 310 that is inflated with fluid or air when a measurement is being taken and deflated when not in use. This feature allows for: (1) prolonged exposure to the patient with little effect on circulation (while in its deflated state); (2) the ability to adjust to different diameter blood vessels in the body; and (3) maximum pressure differential while at the same time feeding back the diameter of the obstruction for flow calculation. The diameter of this sac 310 is determined by measuring the amount of fluid needed to inflate it. Since the radius of the sphere will vary with the cubed-root of its volume, the amount of fluid injected will give the change in radius of the obstruction.

Using Fiber Optic Differential Pressure Measurement To Detect Arterial Blockages (Stenosis)

The catheter illustrated in FIG. 15 is a useful device to detect arterial blockage. By traversing the arteries and monitoring pressure changes an abrupt narrowing, in an artery, of finite length a stenosis 300 FIG. 15 is detectable.

The cause of the pressure differential will be the increase in velocity of the fluid while in, and immediately after the blockage by the Bernoulli effect and the permanent pressure loss due to turbulence in the flow from the stenosis.

By the flow (Bernoulli) equation, the pressure drop between the free-stream flows and the minimum flow area of the stenosis is:

$$\Delta h = 1.3 \times 10^{-2} \cdot q \cdot \frac{\rho f[1 - (d/D)^4]}{d^4}$$

Where:
$\Delta h$=head loss between free stream flow and stenosis flow in mmHg
q=flow rate in cm$^3$/min
ff=fluid density in gr/cm$^3$
d=diameter of flow area through stenosis in cm
D=normal diameter of blood vessel The diameter of the obstruction can be determined by solving for d:

$$d = \frac{x}{1 + (X/D^4)}$$

$$\text{Where: } x = \frac{1.3 \times 10^{-2} \cdot q^2 \rho f}{\Delta h}$$

I claim:

1. A fiber optic fluid differential pressure measuring device comprising a radiant energy emitting means having a predetermined coherence length an optical fiber sensor configured as an interferometer segment mounted on an optic fiber; said sensor interferometer segment causing path deviations of a measuring beam to be greater than the coherence length of the radiant energy emitted from said radiant energy emitting means; a pair of orifices adapted to be in communication with the fluid pressure to be measured, said orifices positioned at each end of the optical fiber sensor segment; means for positioning said optical fiber sensor segment in the fluid to be measured; means for creating constriction in the fluid to be measured spaced between the pair of orifices; a fiber optical demodulator interferometer segment; said demodulator interferometer segment causing the path length of the said measuring beam to be within the coherence length of said radiant energy emitting means; means connecting the optical fiber sensor interferometer segment to the demodulator interferometer segment, said radiant energy emitting means directing radiant energy to the sensor interferometer segment through the optic fiber; and radiant energy detecting means connected to said demodulator interferometer segment.

2. The fiber optic fluid differential pressure measuring device as defined in claim 1, including two optical fiber sensors; two remote demodulation Fabry-Perot interferometer segments and said fiber optical pressure sensitive sensors connected one to each interferometer segment.

3. The fiber optic fluid differential pressure measuring device as defined in claim 1 wherein the radiant energy emitting means comprises an injection laser diode.

4. The fiber optic fluid differential pressure measuring device as defined in claim 1 wherein the radiant energy emitting means comprises a helium neon laser.

5. The fiber optical fluid differential pressure measuring device as defined in claim 1 including a laser; and means for reducing optical feedback to the laser.

6. The fiber optic fluid differential pressure measuring device as defined in claim 5 wherein the means for reducing optical feed back comprises a multimode laser and a remote Fabry-Perot cell with a piezoelectric rod for phase-locked-loop feedback.

7. The fiber optic fluid differential pressure measuring device as defined in claim 5 wherein the means for reducing optical feedback to the laser comprises a polarizer and a one-fourth wave plate located between the laser and the interferometer.

8. The fiber optic fluid differential pressure measuring device as defined in claim 7 further including a polarization rotator.

9. Means for measuring fluid flow in arteries and veins comprising a radiant energy emitting means having a predetermined coherence length a catheter; a single optical fiber; a fiber optic differential fluid pressure sensor configured as an interferometer segment housed in the catheter and mounted on said optical fiber; said sensor segment causing path deviations of a measuring beam to be greater than the coherence length of the radiant energy emitted from said radiant energy emitting means; a pair of orifices, positioned one at each end of the sensor segment; an enlarged zone formed on the catheter spaced between the pair of orifices; a fiber optical demodulator interferometer segment, said demodulator interferometer segment causing the path length of the said measuring beam to be within the coherence length of said radiant energy emitting means; means connecting the optical fiber sensor segment to the demodulator interferometer segment, said radiant energy emitting means directing radiant energy to said sensor segment; and radiant energy detector means connected to said demodulator interferometer segment.

10. The means for measuring fluid flow as defined in claim 9 wherein the enlarged zone is formed by an inflatable balloon.

11. The means for measuring fluid flow in arteries and veins as defined in claim 9 including at least two sensors and at least two remote demodulation Fabry-Perot interferometer segments.

12. The fiber optic fluid flow measuring device as defined in claim 9 wherein the radiant energy emitting means comprises an injection laser diode.

13. The fiber optical Fluid Flow measuring device as defined in claim 9 wherein the radiant energy emitting means comprises a multimode diode laser.

14. The fiber optic fluid flow measuring device as defined in claim 13 including means for reducing optical feedback to the laser.

15. The fiber optic fluid flow measuring device as defined in claim 9 wherein the radiant energy emitting means comprises a helium neon laser.

16. The fiber optic fluid flow measuring device as defined in claim 15 including means for reducing optical feedback to the laser.

* * * * *